United States Patent [19]

Bergeron

[11] Patent Number: 4,987,253
[45] Date of Patent: Jan. 22, 1991

[54] METHOD FOR THE SYNTHESIS OF DESFERRIOXAMINE B AND ANALOGS THEREOF

[75] Inventor: Raymond J. Bergeron, Gainesville, Fla.

[73] Assignee: University of Florida, Gainesville, Fla.

[21] Appl. No.: 352,917

[22] Filed: May 17, 1989

Related U.S. Application Data

[63] Continuation-in-part of Ser. No. 246,152, Sep. 19, 1988, which is a continuation-in-part of Ser. No. 206,319, Jun. 14, 1988.

[51] Int. Cl.$^5$ ............................................. C07C 259/06
[52] U.S. Cl. ..................................... 562/623; 558/390; 558/391; 558/394; 558/446; 558/451; 558/452; 560/312; 564/153
[58] Field of Search ................. 564/153; 558/391, 394, 558/446, 452, 390, 451; 562/623; 560/312

[56] References Cited

U.S. PATENT DOCUMENTS 3,118,823  1/1964  Gaeumann et al. .................. 435/121
3,153,621  10/1984 Gaeumann et al. .................. 435/121

OTHER PUBLICATIONS

Greene, "Protective Groups in Organic Synthesis", pp. 9–15, 50 and 72, [Date unknown], John Wiley & Sons, N.Y., Chichester, Brisbane, Toronto, Singapore.

Primary Examiner—Joseph Paul Brust
Attorney, Agent, or Firm—Kerkam, Stowell, Kondracki & Clark

[57] ABSTRACT

Disclosed is a synthesis of desferrioxamine B and analogs and homologs thereof beginning with the generation of the O-protected N-(4-cyanobutyl)hydroxylamine which is acylated at the O-benzylhydroxylamine nitrogen with either succinic or acetic anhydride. The resulting half-acid amide or amide respectively, is subjected to a series of high yield condensations and reductions which provide desferrioxamine B in 45% overall yield. Finally, a desamino analog of desferrioxamine is prepared in order to demonstrate the synthetic utility of the scheme as applied to desferrioxamine derivatives.

5 Claims, No Drawings

METHOD FOR THE SYNTHESIS OF DESFERRIOXAMINE B AND ANALOGS THEREOF

RELATED APPLICATIONS

This is a continuation-in-part application of Ser. No. 246,152, filed Sept. 19, 1988 which is a continuation-in-part of Ser. No. 206,319, filed June 14, 1988 both now abandoned.

BACKGROUND OF THE INVENTION

1. Field of the Invention

The present invention relates to an improved method for the synthesis of desferrioxamine B and analogs and homologs thereof.

2. Description of the Prior Art

The microbial iron chelator, siderophore, desferrioxamine B [N-(5-(3-((5-aminopentyl)hydroxycarbamoyl)-propionamido)pentyl)-3-((5-(N-hydroxyacetamido)pentyl)carbamoyl)-propionohydroxamic acid] was isolated from Streptomyces pilosus and characterized by Bickel [Helv. Chim. Acta., Vol. 43, p. 2129] in 1960. It is a linear trihydroxamate ligand which forms a very stable hexacoordinate, octahedral [Modell et al, The Clinical Approach to Thalassaemia, Grune and Stratton, London, pp. 217–241 (1984)] complex with Fe(III), $Kf = 1 \times 10^{30} M^{-1}$. The ligand employs its three bidentate hydroxamates units in chelating metal ions.

Although desferrioxamine B will bind a number of different +3 cations, e.g., Al(III), Ga(III), Cr(III), it exhibits a high specificity for Fe(III), and is utilized by Streptomyces pilosus for the acquisition of iron from the environment. Because of the ligand's metal selectivity and low toxicity it has been employed in the treatment of several iron overload diseases, e.g., thalassaemia [Development of Iron Chelators for Clinical Use (Martell et al, Eds.) Elsevier/North Holland, New York (1981)]. However, desferrioxamine B does not offer a completely satisfactory solution to the iron overload problem. The drug is cleared by the kidneys and has a very short half-life in the body, and thus the patient must be maintained on constant infusion therapy. It is not orally effective. Because of these shortcomings, investigators have explored the potential of other ligands as therapeutic iron chelators. To date these investigations have not included modification of the desferrioxamine molecule simply because of the lack of high yield or facile approaches to the synthesis of the molecule.

Desferrioxamine B was first synthesized in 1962 by Prelog et al [Helv. Chim. Acta., Vol. 75, p. 631 (1962)]. However, because of the number of steps in the synthesis and the low yield of the sequence, the method does not enable the production of large quantities of the chelator or its analogs. A retrosynthetic analysis of the ligand reveals that the desferrioxamine molecule is made up of two fundamental units, 1-amino-5(N-hydroxyamino)-pentane and succinic acid. The key to its synthesis is the production of this amino-hydroxyaminopentane unit and its condensation with succinic acid. Prelog approached this problem beginning with the starting material 1-amino-5-nitropentane, an amine which was accessible in only 46% yield [Bickel et al, Helv. Chim. Acta., Vol. 43, p. 901 (1960)]. This compound was next N-carbobenzoxylated and the terminal nitro group reduced to the corresponding hydroxyamino group. This key intermediate was condensed with succinic acid followed by a series of other dicyclohexylcarbodiimide catalyzed acylations along with several reductions to produce desferrioxamine B. The overall yield of this eleven step sequence was 6%.

It is an object of the present invention to provide novel, improved high yield methods for the production of desferrioxamine B and homologs and analogs thereof.

SUMMARY OF THE INVENTION

The above and other objects are realized by the present invention which provides a method for synthesizing desferrioxamine B or homologs thereof comprising (a) reacting an aldehyde having the formula, $NC(CH_2)_nCHO$ (1) wherein n is an integer from 1 to 10 with an aminating agent comprising an O-substituted oxyamine wherein the substituent on the O is an hydroxyl protecting group such as O-benzyl to produce an oxime having the formula, $NC(CH_2)_nCH=NOCH_2C_6H_5$ (2) and reducing the oxime to produce a hydroxylamine having the formula, $NC(CH_2)_{n+1}NHOCH_2C_6H_5$ (3), Alternatively, and more efficiently, the hydroxylamine (3) may be prepared by converting the O-substituted oxyamine (e.g., O-benzylhydroxylamine) to an N-protected intermediate, e.g., its N-(tertbutoxycarbonyl) derivative $[C_6H_5\text{-}CH_2ONH\text{-}COOC(CH_3)_3$ (A)]. The carbamate (A) is then N-alkylated with, e.g., haloalkylnitrile halo-$(CH_2)_{n+1}CN$ wherein halo is halogen to produce the intermediate nitrile=

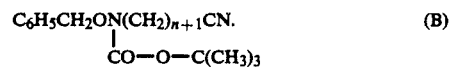

The protective t-butoxycarbonyl group is then cleaved, e.g., by exposure of the nitrile (B) to trifluoroacetic acid, to produce the hydroxylamine (3).

(b) condensing a hydroxylamine (3) with an anhydride having the formula,

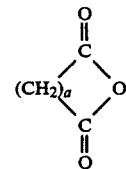

wherein a is an integer from 1 to 6 to produce a compound having the formula,

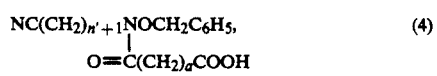

wherein n' is an integer from 1 to 10, (c) condensing a hydroxylamine (3) with an anhydride having the formula $(RCO)_2O$, wherein R is an alkyl group having from 1 to 10 carbon atoms or any aryl group to produce a compound having the formula,

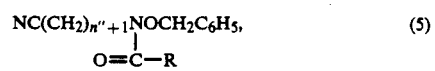

wherein n" may be the same as or different from n' and is an integer from 1 to 10, (d) reducing the compound (5) to produce an amine having the formula,

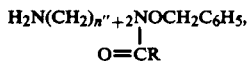
(6)

(e) condensing compounds (4) and (6) to produce a compound having the formula,

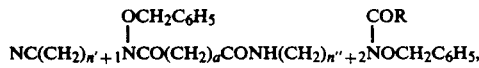
(7)

(f) reducing (7) to produce an amine having the formula,

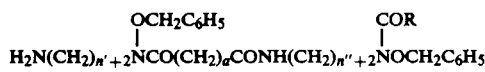
(8)

(g) condensing amine (8) with compound (4) to produce a nitrile having the formula,

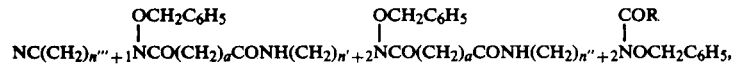
(9)

wherein n''' is an integer from 1 to 10 and may be the same as or different from n' and n", (h) reducing the nitrile (9) to produce a hydroxamate having the formula,

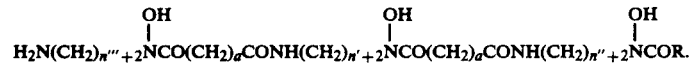
(10)

A further embodiment of the present invention relates to a method for synthesizing a tetracoordinate hydroxamate comprising:

(a) reacting O-benzylhydroxylamine with an aldehyde having the formula $NC(CH_2)_nCHO$ (1) wherein n is an integer from 1 to 10 to produce an oxime having the formula, $NC(CH_2)_nCH=NOCH_2C_6H_5$ (2) and reducing the oxime to produce a hydroxylamine having the formula $NC(CH_2)_{n+1}NHOCH_2C_6H_5$ (3), (b) condensing the hydroxylamine (3) with an anhydride having the formula,

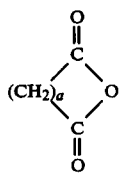

wherein a is an integer from 1 to 6 to produce a compound having the formula,

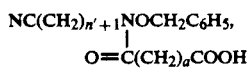
(4)

wherein n' is an integer from 1 to 10.

(c) condensing a hydroxylamine (3) with an anhydride having the formula $(RCO)_2O$, wherein R is an alkyl group having from 1 to 10 carbon atoms or any aryl group to produce a compound having the formula,

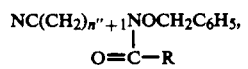
(5)

wherein n" may be the same as or different from n' and is an integer from 1 to 10, (d) reducing the compound (5) to produce an amine having the formula,

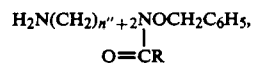
(6)

(e) condensing compounds (4) and (6) to produce a compound having the formula,

(7)

(f) hydrogenating (7) to produce a tetracoordinate hydroxamate having the formula,

(11)

wherein n, n', n", a and R have the meanings set forth above.

A still further embodiment of the invention is a method for synthesizing an octacoordinate hydroxamate comprising, (a) reacting O-benzylhydroxylamine with an aldehyde having the formula, $NC(CH_2)_nCHO$ (1), wherein n is an integer from 1 to 10 to produce an oxime having the formula, $NC(CH_2)_nCH=NOCH_2C_6H_5$ (2), and reducing the oxime to produce a hydroxylamine having the formula $NC(CH_2)_{n+1}NHOCH_2C_6H_5$ (3), (b) condensing a hydroxylamine (3) with an anhydride having the formula,

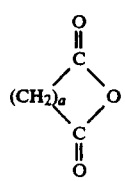

wherein a is an integer from 1 to 6 to produce a compound having the formula,

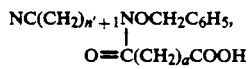
(4)

wherein n' is an integer from 1 to 10, (c) condensing a hydroxylamine (3) with an anhydride having the formula (RCO)₂O, wherein R is an alkyl group having from 1 to 10 carbon atoms or any alkyl group to produce a compound having the formula,

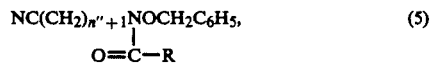
(5)

wherein n'' may be the same as or different from n' and is an integer from 1 to 10, (d) reducing the compound (5) to produce an amine having the formula,

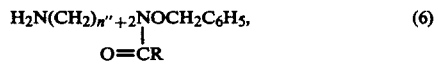
(6)

(e) condensing compounds (4) and (6) to produce a compound having the formula,

(7)

(f) reducing (7) to produce an amine having the formula,

(8)

(g) condensing amine (8) with compound (4) to produce a nitrile having the formula,

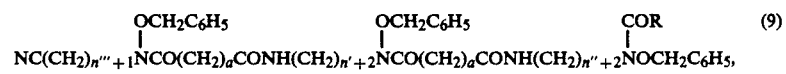
(9)

wherein n''' is an integer from 1 to 10 and may be the same as or different from n' and n'', (h) reducing the nitrile (9) to produce an amine having the formula,

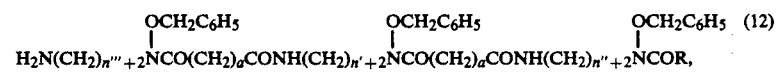
(12)

(i) condensing (12) with an equivalent of (4) to produce a nitrile having the formula,

(13)

(j) reducing (13) to produce an octacoordinate hydroxamate of the formula, wherein $n^{iv}$ is an integer from 1 to 10 and may be the same as or different from n, n', n'' and n''', a and R have the meanings set forth above.

A final embodiment of the invention is a method for synthesizing alkyl or aryl connected hydroxamates, e.g., N-[5-[3-[heptylhydroxycarbamoyl]propionamido]-pentyl]-3-[[5-(N-hydroxyacetamido)-pentyl]carbamoyl]propionohydroxamic acid comprising:

(a) reacting O-benzylhydroxylamine with an aldehyde of the formula R'—CHO, wherein R' is alkyl having 1 to 20 carbon atoms; G—Y—(CH₂)ₓ—, wherein G is a removable protecting group (e.g., t-butoxycarbonyl), Y is —O— or —NH— and x is an integer from 1 to 20; or

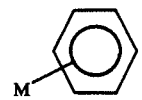

wherein M is —OG, —OR₁ (wherein R₁ is an alkyl group having from 1 to 20 carbon atoms), —COOH, or —NHG to produce an oxime having the formula, R'CH=NOCH₂C₆H₅ (15) and reducing (15) to produce a hydroxylamine having the formula R'CH₂NHOCH₂C₆H₅ (16), (b) condensing (16) with an anhydride having the formula,

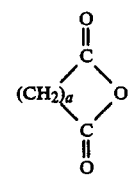

wherein a is an integer from 1 to 6 to produce a compound having the formula,

(17)

(c) condensing (17) with (6), (8) or an amine having the formula,

(14)

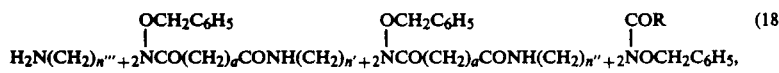(18)

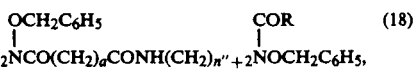

to produce compounds of the formulae:

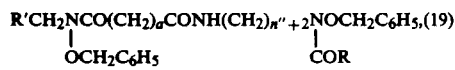(19)

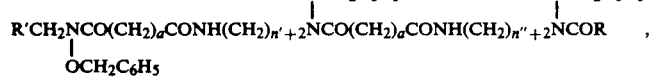(20)

and

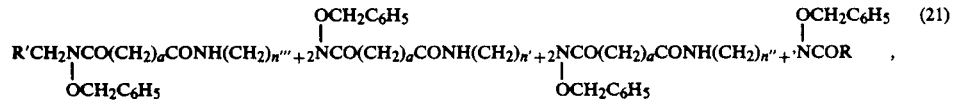(21)

respectively, (d) reducing (19), (20) or (21) to produce the corresponding hydroxamate having the formulae:

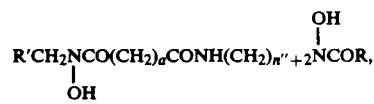(22)

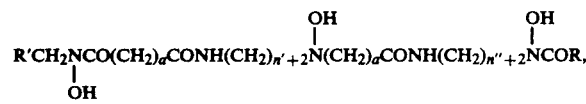(23)

or

(24)

DETAILED DESCRIPTION OF THE INVENTION

The synthesis of desferrioxamine B according to the invention begins with the production of the protected N-(4-cyanobutyl)-hydroxylamine [compound (3) above] where the O-protecting group is benzyl. It will be understood by those skilled in the art that any suitable aminating agent comprising an O-substituted oxamine [Z—O—NH$_2$], wherein Z is a removable hydroxyl protecting group, may be employed in the practice of the invention. Suitable such oxyamines include t-butoxyamine, 2-tetrahydropyranyloxyamine, O-benzylhydroxylamine, substituted O-benzylhydroxylamine, etc. The above reaction schemes illustrate the use of O-benzylhydroxylamine.

In the cases where t-butoxyamine and 2-tetrahydropyranyloxyamine are employed, the t-butyl or tetrahydropyranyl protecting groups are preferably removed by exposure of the protected compounds to trifluoroacetic acid or hydrochloric acid hydrolysis, respectively.

In the examples set forth below the invention is illustrated using O-benzylhydroxylamine. The compound O-benzyl-N-(4-cyanobutyl)-hydroxylamine (3) was prepared in 85% yield by the condensation of 4-cyanobutanal [Izawa et al, Bull. Chem. Soc., Jap., Vol. 52, pp. 555–558 (1979)] (1) with the hydrochloride salt of O-benzylhydroxylamine followed by reduction of the resulting oxime (2) [Borch et al, J. Am. Chem. Soc., Vol. 93, p. 2897 (1971)] to the hydroxylamine (3).

More preferably, the hydroxylamine (3) is prepared by converting O-benzylhydroxylamine hydrochloride to its crystalline N-(tert-butoxycarbonyl) derivative (A) [Ramasamy et al, J. Org. Chem., Vol. 46, pp. 5438–5441 (1981); Lee et al, J. Org. Chem., Vol. 48, pp. 24–31 (1983)]. This is preferably accomplished by reaction of the hydroxylamine salt with di-tert-butyl dicarbonate in triethylamine/aqueous tetrahydrofuran. The carbamate (A) is obtained in 97% yield and is then N-alkylated with 5-chlorovaleronitrile in DMF/NaH/NaI to produce the intermediate nitrile (B) in 87% yield. Exposure of (B) to trifluoroacetic acid results in a collapse of (B) to produce carbon dioxide, isobutylene and (3) in 75% yield. This alternative route to (3) is preferred since 4-cyanobutanol is accessible only in low yield and is somewhat unstable.

In the next step (3) is condensed with succinic anhydride to produce the half acid amide (4) in 88% yield and also with acetic anhydride to generate the corresponding cyano acetyl amide (5) quantitatively. The cyanoamide (5) is next hydrogenated to the amine (6) in 82% yield. The reaction is preferably carried out in methanol-ammonia utilizing prewashed nickel catalyst [Albert et al, J. Chem. Soc., Vol. 91, 91, p. 4606 (1969)]. It has been determined that if the catalyst is not first washed with water to remove residual sodium hydroxide the reaction mixture includes a number of unwanted products. The amine (6) is then condensed with the half acid amide (4) in 88% yield employing a condensing agent, e.g., dicyclohexylcarbodiimide. The resulting nitrile (7) is then reduced to the corresponding amine (8) in 82% yield, employing the nickel catalyst described above. The amine (8) is treated with the half acid amide (4), preferably in the presence of dicyclohexylcarbodiimide and the resulting nitrile (9) is isolated in 88% yield. The nitrile (9) is then reduced to the final product, desferrioxamine B (10) in 84% yield, e.g., utilizing 10% Pd/C in 0.1M HCl in methanol.

This synthesis also lends itself to modification of the desferrioxamine backbone. For example, the synthesis can be terminated at the nitrile (7) and this compound reduced to the corresponding tetracoordinate ligand, e.g., by exposing the compound to hydrogen over palladium. Alternately, the octacoordinate ligand can be generated by first reducing the nitrile of the desferrioxamine precursor (9), followed by condensation of the product with a second equivalent of (4) and then by reduction, e.g., with hydrogen over palladium.

A desamino analog can be prepared beginning with heptanal. This aldehyde is treated with the hydrochloride salt of O-benzylhydroxylamine (1a) and the resulting oxime (2a) reduced, e.g., with sodium cyanoborohydride to produce the O-benzyl-N-heptylhydroxylamine (3a) in 22% yield.

The hydroxylamine (3a) is next condensed with succinic anhydride to generate the half acid amide (4a) in 83% yield. This amide is then condensed with amine (8) from the above synthesis. The condensation product (6a) is finally reduced, e.g., with hydrogen over palladium providing the desamino analog (7a) in 86% yield.

Thus, it is apparent that the synthetic schemes described above are viable methods for the total synthesis of desferrioxamine B as well as a variety of its homologs and analogs.

The invention is illustrated by the following non-limiting examples.

EXAMPLES

4-Cyanobutanal (1) was prepared from 35.1 g (0.16 mol) of the 3-acylthiazolidine-2-thione according to the method of Izawa, supra. The aldehyde was purified by distillation at 83°–84° C. (2 mm) [Brown, supra] to give 9.7 g (61%) of product. $^1$H NMR (CDCl$_3$): δ 1.80–2.15 (m, 2H), 2.5 (t, 2H, J=6.3 Hz), 2.67 (t, 2H, J=6.3 Hz), 9.9 (s, 1H), identical with literature values [Osei-Twum et al, J. Org. Chem., Vol. 49, p. 336 (1984)]; IR (CHCl$_3$) 3500, 2940, 2895, 2825, 2700, 2240, 1725, 1610, 1445, 1420, 1360 cm$^{-1}$.

O-Benzyl-N-(4-cyanobutyl)hydroxylamine (3). O-Benzylhydroxylamine hydrochloride (4.7 g, 29.7 mmol) was mixed with 5 mL of water and 11 mL of methanol at 0° C. and the apparent pH adjusted to 4.7 using 6N potassium hydroxide. The aldehyde, 4-cyanobutanal (1), [Izawa, supra] (2.6 mL, 27 mmol) was added to the hydroxylamine and the mixture allowed to warm to room temperature. The pH was maintained by the addition of further 6N potassium hydroxide. After 1 h, the reaction was cooled to 0° C., and sodium cyanoborohydride (1.26 g, 20 mmol) was added. The pH was adjusted to 3 and maintained by addition of saturated hydrogen chloride in methanol. When the pH stabilized, the reaction was warmed to room temperature and stirred for 3 h at a pH of 3. The reaction mixture was then poured into ether and made basic with 6N potassium hydroxide. The aqueous layer was extracted with ether (3×50 mL). The extracts were combined, washed with brine, and dried over magnesium sulfate. The solvents were removed and the resulting liquid distilled at 150°–151° C. (0.6 mm) to give 4.65 g (84%) of (3): $^1$H NMR (CDCl$_3$): δ 1.56–1.85 (m, 4H), 2.20–2.45 (m, 2H), 2.85–3.10 (m, 2H), 4.7 (s, 2H), 5.53 (t, 1H), 7.4 (s, 5H); IR (CHCl$_3$): 3040, 2930, 2860, 2240, 1500, 1450, 1430, 1360, 1210; Anal. Calcd. for $C_{12}H_{16}N_2O$: C, 70.54; H, 7.91. Found: C, 70.51; H, 7.91.

O-Benzyl-N-(tert-butoxycarbonyl)hydroxylamine (A) was prepared according to the literature methods (Ramasamy et al and Lee et al) from O-benzylhydroxylamine hydrochloride and di-tert-butyl dicarbonate in NEt$_3$, aqueous THF: m.p. 46°–48° C. (lit. 45°–47° C.).

O-Benzyl-N-(tert-butoxycarbonyl)-N-(4-cyanobutyl)-hydroxylamine (B). Sodium iodide (84 mg, 0.56 mmol) and then sodium hydride (80% oil dispersion, 0.49 g, 16.3 mmol) were added to (A) (2.68 g, 12.0 mmol) in dry DMF (40 mL). After stirring 15 min, 5-chlorovaleronitrile (1.5 mL, 13.3 mmol) was added, and the suspension heated at 80°–85° C. for 4 h under argon. After cooling, the reaction was quenched with H$_2$O (100 mL), then extracted with ether (4×75 mL). The combined organic layers were washed with 100 mL each of 1% aqueous Na$_2$SO$_3$, H$_2$O and brine and then concentrated to give 4.39 g crude product. Column chromatography with 4.5% EtOAc/CHCl$_3$ produced 3.17 g of (B) (87% yield): NMR δ 1.5–1.75 (s+m, 13 H), 2.3 (t, 2 H), 3.4 (t, 2 H), 4.77 (s, 2 H), 7.3 (s, 5 H). Anal. Calcd for $C_{17}H_{24}N_2O_3$: C, 67.08; H, 7.95; N, 9.20. Found: C, 67.19; H, 7.99; N, 9.11.

O-Benzyl-N-(4-cyanobutyl)hydroxylamine (3). Trifluoroacetic acid (TFA, 16 mL) was added to (B) (2.59 g, 8.51 mmol), and the solution stirred at room temperature for 20 min (Drierite tube). Excess TFA was removed on the rotovap, saturated NaHCO$_3$ (50 mL) was added and the product was extracted into ether (3×50 mL). After a brine wash (50 mL), the organic extracts were concentrated to yield 1.77 g crude product. Column chromatography with 3% EtOH/CHCl$_3$ furnished 1.31 g of (3) (75% yield), which has been previously prepared: NMR δ1.5–1.7 (m, 4 H), 2.16–2.35 (m, 2 H), 2.78–2.98 (m, 2 H), 4.66 (s, 2 H), 5.45 (br s, 1 H), 7.28 (s, 5 H).

N-(4-Cyanobutyl)-N-(benzyloxy)succinamic Acid (4). A flask was charged with 2.8 g (13.7 mmol) of (3) in 23 mL of pyridine and 2.1 g (20.8 mmol) of succinic anhydride, initially heated at 100° C. for 1.5 h and then allowed to cool to room temperature and to stir overnight. The pyridine was removed under vacuum and the residue was dissolved in a minimal amount of chloroform and filtered. The chloroform was removed, and the residue was dissolved in ether, which was extracted three times with 20% potassium bicarbonate (3×50 mL). The aqueous solutions were combined, acidified and extracted with ether. This solution was dried over anhydrous sodium sulfate, filtered and evaporated. The residue was then chromatographed on 70–230 mesh silica gel by eluting with 5% methanol in chloroform to give 4.12 g (98%) of product: $^1$H NMR (CDCl$_3$): δ 1.56–1.7 (m, 2H), 1.7–1.97 (m, 2H), 2.36 (t, 2H), 2.60–2.80 (m, 4H), 3.68 (t, 2H), 4.85 (s, 2H), 7.4 (s, 5H); IR (CHCl$_3$): 3670, 2930, 2240, 1710, 1650, 1415, 1200; Anal. Calcd. for $C_{16}H_{20}N_2O_4$: C, 63.17; H, 6.64. Found: C, 63.36; H, 6.74.

N-(4-Cyanobutyl)-N-(benzyloxy)acetamide (5). A solution of 2.6 g (12.75 mmol) of (3), 17.24 mL of pyridine and 17.2 mL of acetic anhydride were stirred under argon at room temperature for 24 h. At the end of this period, the excess pyridine and acetic anhydride were removed by vacuum (0.05 mm). The resulting oil was taken up in chloroform, which was extracted with 1N hydrochloric acid (2×50 mL), saturated sodium bicarbonate (2×50 mL), and brine (50 mL) and then dried over anhydrous sodium sulfate. The solution was filtered, and the solvent was removed to yield 3.14 g (100%) of product as a light oil: $^1$H NMR (CDCl$_3$): δ 1.5–1.9 (m, 4H), 2.1 (s, 3H), 2.26 (t, 2H), 3.67 (t, 2H), 4.84 (s, 2H), 7.41 (s, 5H); IR (CHCl$_3$): 3040, 2940, 2880, 2240, 1650, 1450, 1410; Anal. Calcd. for C$_{14}$H$_{18}$N$_2$O$_2$: C, 68.26; H, 7.38. Found: C, 68.25; H, 7.44.

N-(5-Aminopentyl)-N-(benzyloxy)acetamide (6). A 250 ml Parr shaker bottle was charged with 2.6 g (damp) Raney nickel, 1.4 g (5.7 mmol) of (5), 15 mL of ammonia-saturated methanol, and 4 mL of saturated ammonium hydroxide. The bottle was cooled in an ice bath and anhydrous ammonia was allowed to bubble through the solution for 10 min in order to insure saturation. The bottle was pressurized to 50 psi with hydrogen and the reaction was allowed to proceed with shaking for 3 h. At the end of this period, the catalyst was removed by filtration through celite and the solvents were evaporated. The crude material was purified by chromatography on 70-230 mesh silica gel, which was prewashed with solvent to remove soluble particulates. Elution with 1% ammonium hydroxide in methanol gave a 1.25 g (88%) yield of desired material: $^1$H NMR (CDCl$_3$): δ 1.2–1.9 (m, 8H), 2.1 (s, 3H), 2.53–2.83 (m, 2H), 3.64 (t, 2H), 4.80 (s, 2H), 7.4 (s, 5H); IR (CHCl$_3$): 3600, 3420, 2920, 2860, 2220, 1650, 1400; HRMS calcd. for C$_{14}$H$_{22}$N$_2$O$_2$ 250.1680. Found: 250.1670; Anal. Calcd. for C$_{14}$H$_{22}$N$_2$O$_2$: C, 67.15; H, 8.87. Found: C, 66.71; H, 8.79.

N-(4-Cyanobutyl)-3-[[5-(N-benzyloxy)acetamido)-pentyl]carbamoyl]-O-benzylpropionohydroxamic Acid (7). A mixture of 28 mL chloroform, 1.46 g (4.79 mmol) of (4), 1 g (4 mmol) of (6), 1.24 g (6 mmol) of DCC and 70 mg of DMAP was cooled to 0° C. for 0.5 h, allowed to warm to room temperature and stirred for 24 h. The reaction mixture was again cooled to 0° C. and filtered. The resulting oil was chromatographed on 70-230 mesh silica gel by eluting with 2.5% methanol in chloroform to yield 2.1 g (98%) of product: $^1$H NMR (CDCl$_3$): δ 1.2–1.9 (m, 10H), 2.1 (s, 3H), 2.3–2.6 (m, 4H), 2.7–3.0 (m, 2H), 3.10–3.40 (m, 2H), 3.55–3.80 (m, 4H), 4.83 (s, 2H), 4.9 (s, 2H), 6.1–6.3 (m, 1H), 7.45 (s, 10H); IR (CHCl$_3$): 3665, 3450, 3350, 2940, 2880, 2250, 1660, 1520, 1410; Anal. Calcd. for C$_{30}$H$_{40}$N$_4$O$_5$: C, 67.14; H, 7.51. Found: C, 66.70; H, 7.58.

N-(5-Aminopentyl)-3-[[5-(N-benzyloxyacetamido)-pentyl]carbamoyl]-O-benzylpropionohydroxamic Acid (8). A 250 mL Parr shaker bottle was charged with 1.28 g of damp Raney nickel, 1.22 g (2.27 mmol) of (7), 3 mL of ammonia saturated methanol and 0.7 mL of ammonium hydroxide. The bottle was cooled in an ice bath and anhydrous ammonia was bubbled through the solution for 25 min to insure saturation. The bottle was placed on the shaker and pressurized to 50 psi with hydrogen. The reaction was allowed to proceed for 2.5 h. The catalyst was filtered off, the solvent was removed and the crude material was chromatographed on 70-230 mesh silica gel with 0.7% ammonium hydroxide in methanol as eluant to give 1 g (82%) of product: $^1$H NMR (CDCl$_3$): δ 1.17–1.40 (m, 4H), 1.40–1.60 (m, 4H), 1.60–1.77 (m, 4H), 2.1 (s, 3H), 2.20–2.60 (m, 4H), 2.60–2.75 (m, 2H), 2.75–2.87 (m, 2H), 3.12–3.30 (m, 2H), 3.5–3.77 (m, 4H), 4.80 (s, 2H), 4.88 (s, 2H), 6.15–6.37 (m, 1H), 7.63 (s, 10H); IR (CHCl$_3$): 3620, 3440, 2940, 2860, 2240, 1655, 1445, 1410 cm$^{-1}$; Anal. Calcd. for C$_{30}$H$_{44}$N$_4$O$_5$.H$_2$O: C, 64.49; H, 8.30. Found: 64.50; H, 8.14.

N-[5-[3-[(4-Cyanobutyl)(benzyloxy)carbamoyl]propionamido]pentyl]-3-[[5-(N-benzyloxyacetamido) pentyl]carbamoyl]-O-benzylpropionohydroxyamic Acid (9). A mixture of 0.33 g (1.07 mmol) of (4), 0.58 g (1.07 mmol) of (8), 13 mg of DMAP, and 5.3 mL of chloroform was cooled to 0° C. and 0.28 g (1.35 mmol) DCC was added. After 10 min, the reaction was allowed to warm to room temperature and stirred for 12 h. The reaction was then cooled at 0° C. and filtered. The solvent was removed and the crude material was chromatographed on 70-230 mesh silica gel with 2.5% MeOH in chloroform as eluant to give 0.78 g (88% of product): $^1$H NMR (CDCl$_3$): δ 1.4–1.59 (m, 4H), 1.59–1.70 (m, 6H), 1.70–1.85 (m, 6H), 2.1 (s, 3H), 2.35 (t, 2H), 2.40–2.55 (m, 4H), 2.75–2.90 (m, 4H), 3.18–3.28 (m, 4H), 3.6–3.7 (m, 6H), 4.8 (s, 2H), 4.82 (s, 2H), 4.84 (s, 2H), 6.20–6.75 (m, 2H), 7.4 (s, 15H); IR (CHCl$_3$): 3680, 3440, 3340, 2990, 2940, 2870, 2250, 1660, 1520, 1455, 1415 cm$^{-1}$; Anal. Calcd. for C$_{46}$H$_{62}$N$_6$O$_8$: C, 66.30; H, 7.68. Found: C, 66.44; H, 7.66.

Desferrioxamine B Hydrochloride (10). Compound (9), (0.165 g, 0.2 mmol) was reduced in 68 mL methanol, 2.7 mL of 0.1N hydrochloric acid and 0.27 g of 10% palladium on carbon. The hydrogenation was carried out at one atmosphere of hydrogen for 7.5 hrs. The solution was filtered, the solvents were removed and the residue was washed with cold methanol, and then chloroform to give 0.1 g (84%) of product. This material had a mp of 167°–168° C., [Prelog, supra] and was identical to an authentic sample by 300 MHz NMR [sample of desferrioxamine B supplied by Dr. Heinrich H. Peter at Ciba-Geigy, Basel, Switzerland].

O-Benzyl-N-heptylhydroxylamine (3a). O-Benzylhydroxylamine hydrochloride (1a) (13.37 g, 83.74 mmol) was dissolved in 31 mL of methanol and 14 mL of water at 0° C. and the apparent pH adjusted to 4.7 using 6N potassium hydroxide. Heptanal (10.2 mL, 76 mmol) was added, and the pH was maintained at 4.7 while the reaction warmed to room temperature. After the pH change stabilized, the mixture was again cooled to 0° C. and 3.54 g (56.31 mmol) of sodium cyanoborohydride was added. The pH was then lowered to just below 3 and maintained there by the addition of 2N hydrogen chloride in methanol. When the pH change had stabilized, the solution was stirred at pH 3 for 3 h at room temperature. The mixture was then poured into ether (100 mL) and brine (50 mL), and enough 6N potassium hydroxide was added to bring the pH to 9. The aqueous layer was extracted with ether (3×50 mL) and the ether solutions were combined and dried over magnesium sulfate. The solvents were then removed, and the resulting oil distilled at 110°–112° C. (0.1 mm) to give 3.6 g (22%) of (3a): $^1$H NMR (CDCl$_3$): δ 0.7–1.05 (m, 3H), 1.05–1.73 (m, 10H), 2.92 (t, 2H), 4.7 (s, 2H), 5.3–5.7 (m, 1H), 7.4 (s, 5H); HRMS calcd. for C$_{14}$H$_{23}$NO: 221.1778. Found: 221.1721.

N-Heptyl-N-(benzyloxy)succinamic Acid (4a). A solution of (3a) (2.09 g, 9.44 mmol), and succinic anhydride (1.42 g, 14.15 mmol), in 16 mL of pyridine was stirred at room temperature for 12 h. The pyridine was next removed by vacuum and the resulting material was dissolved in a minimal amount of chloroform. The solution was cooled to 0° C. and filtered. The organic solution was evaporated, and the residue was taken up in ether. The ether solution was extracted with 20% potassium bicarbonate (3×100 mL). The resulting aqueous solution was acidified and extracted with ether (3×100 mL). The ether solution was dried over anhydrous sodium sulfate and the solvent was removed. The residue was then chromatographed on 70–230 mesh silica gel by eluting with 5% methanol in chloroform to give 2.52 g (83%) of product: $^1$H NMR (CDCl$_3$): δ 0.8–1.1 (m, 3H), 1.1–1.5 (m, 8H), 1.5–1.85 (m, 2H), 2.6–2.8 (m, 4H), 3.63 (t, 2H), 4.9 (s, 2H), 7.4 (s, 5H): HRMS calcd for C$_{18}$H$_{27}$NO$_4$: 321.1938. Found: 321.1952.

N-[5-[3-[Heptylbenzyloxycarbamoyl]propionamido]-pentyl-3-[[5-(N-benzyloxyacetamido)pentyl]carbamoyl]-O-benzylpropionohydroxamic Acid (6a). The acid (4a) (0.749 g, 2.3 mmol) and (8) (1.11 g, 2.1 mmol) were dissolved in 11 mL of anhydrous dichloromethane. To this were added 0.6 g (2.9 mmol) of dicyclohexylcarbodiimide and 32 mg (0.26 mmol) of dimethylaminopyridine, and the solution was stirred at room temperature for 20 h. The reaction mixture was cooled to 0° C. and filtered. The solvent was removed and the crude material was purified by chromatography on 70–230 mesh silica gel by eluting with 2% methanol in chloroform to give 1.3 g (73%) of product: $^1$H NMR (CDCl$_3$): δ 0.70–1.05 (m, 3H), 1.05–1.9 (m, 22H), 2.1 (s, 3H), 2.25–2.64 (m, 4H), 2.64–3.0 (m, 4H), 3.0–3.4 (m, 4H), 3.5–3.8 (m, 6H), 4.83 (s, 2H), 4.87 (s, 4H), 6.2–6.5 (m, 2H), 7.4 (s, 15H): FABMS calcd. for C$_{48}$H$_{69}$N$_5$O$_8$: 843. Found: 843.

N-[5-[3-[Heptylhydroxycarbamoyl]propionamido]-pentyl]-3-[[5-(N-hydroxyacetamido)-pentyl]carbamoyl]propionohydroxamic Acid (7a). The acid (6a) (0.49 g, 0.58 mmol) was dissolved in 8.5 mL of methanol and 50 mg of 10% Pd/C added. The hydrogenation was carried out overnight at one atmosphere of hydrogen, the reaction mixture was filtered and the solid was washed with hot methanol. Evaporation of the methanol gave 0.284 g (85%) of product: $^1$H NMR (DMF-d$_7$): δ 0.64–0.9 (m, 3H), 0.9–1.7 (m, 22H), 2.0 (s, 3H), 2.2–2.5 (m, 4H), 2.6–2.8 (m, 4H), 2.9–3.2 (m, 4H), 3.3–3.6 (m, 6H), 9.7–9.95 (m, 3H): FABMS calcd. for C$_{27}$H$_{51}$N$_5$O$_8$: 573. Found: 574 (M+1).

It will be apparent to those skilled in the art, having been exposed to the present description of the invention, that the tetra-, and octa-coordinate hydroxamates and the alkyl and aryl connected hydroxamates may be prepared following the same procedures as set forth in the above examples.

The above-described homologs of desferrioxamine B, i.e., formulae (10), possess the same chemical and therapeutical characteristics and are useful for the same application as desferrioxamine B.

The tetracoordinate hydroxamates of formulae (11) are powerful copper chelators and are particularly useful in the treatment of Wilson's disease.

The octa-coordinate hydroxamates of formulae (14) are useful for chelating plutonium, americium and thorium and find application as therapeutic decontaminants for these metals.

The alkyl and aryl connected hydroxamates of formulae (22), (23) and (24) are useful for the same purposes as the above-described chelators but, because of their greater degree of lipophilicity they will exhibit longer residence times in patients treated therewith than the latter.

The chelators described and claimed herein may be employed in the same manner for therapeutic purposes as is practical with conventional pharmaceutical chelators.

I claim:

1. A method for synthesizing desferrioxamine B or a homolog thereof having the formula

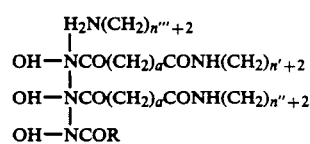

comprising:
(a) reacting an aldehyde having the formula NC(CH$_2$)$_n$CHO (1) wherein n is an integer from 1 to 10 with an aminating agent having the formula Z—O—NH$_2$ wherein Z is an hydroxyl protecting group to produce an oxime having the formula NC(CH$_2$)$_n$CH=NOZ (2) and reducing the oxime to produce a hydroxylamine having the formula NC(CH$_2$)$_{n+1}$NHO—Z (3), or (a-1) reacting an hydroxylamine having the formula Z—ONH—Q (A), wherein Z is an hydroxyl protecting group and Q is an amino protecting group, with an N-alkylating agent having the formula halo-(CH$_2$)$_{n+1}$CN, wherein halo is halogen to produce a nitrile having the formula

and cleaving Q therefrom to produce said hydroxylamine (3), (b) condensing said hydroxylamine (3) with an anhydride having the formula

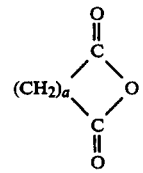

wherein a is an integer from 1 to 6 to produce a compound having the formula

wherein n' is an integer from 1 to 10, (c) condensing said hydroxylamine (3) with an anhydride having the formula (RCO)$_2$O, wherein R is an alkyl group having from 1 to 10 carbon atoms or an aryl group to produce a compound having the formula

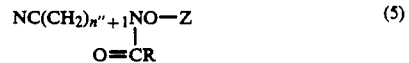

wherein n" may be the same as or different from n' and is an integer from 1 to 10, (d) reducing said compound (5) to produce an amine having the formula

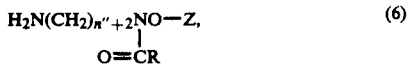
(6)

(e) condensing said compounds (4) and (6) to produce a compound having the formula

(7)

(f) reducing said compound (7) to produce an amine having the formula

(8)

(g) condensing said amine (8) with said compound (4) to produce a nitrile having the formula

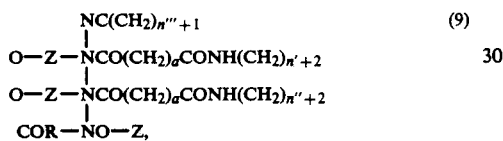
(9)

wherein n''' is an integer from 1 to 10 and may be the same as or different from n' and n", and (h) reducing said nitrile (9) to produce said hydroxamate having the formula

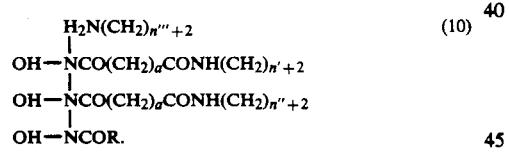
(10)

2. The method of claim 1 for synthesizing desferrioxamine B wherein n''' is 3, a is 2, n' is 3, n" is 3 and R is $CH_3$.

3. A method for synthesizing a tetracoordinate hydroxamate having the formula

(a) reacting an aldehyde having the formula $NC(CH_2)_nCHO$ (1) wherein n is an integer from 1 to 10 with an aminating agent having the formula $Z-O-NH_2$ wherein Z is an hydroxyl protecting group to produce an oxime having the formula $NC(CH_2)_nCH=NO-Z$ (2) and reducing the oxime to produce a hydroxylamine having the formula $NC(CH_2)_{n+1}NHO-Z$ (3), or (a-1) reacting an hydroxylamine having the formula $Z-ONH-Q$ (A), wherein Z is an hydroxyl protecting group and Q is an amino protecting group, with an N-alkylating agent having the formula $halo-(CH_2)_{n+1}CN$, wherein halo is halogen to produce a nitrile having the formula

(B)

and cleaving Q therefrom to produce said hydroxylamine (3), (b) condensing said hydroxylamine (3) with an anhydride having the formula

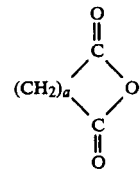

wherein a is an integer from 1 to 6 to produce a compound having the formula

(4)

wherein n' is an integer from 1 to 10, (c) condensing said hydroxylamine (3) with an anhydride having the formula $(RCO)_2O$, wherein R is an alkyl group having from 1 to 6 carbon atoms or an aryl group to produce a compound having the formula

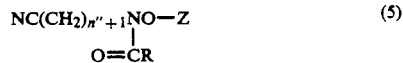
(5)

wherein n" may be the same as or different from n' and is an integer from 1 to 10, (d) reducing said compound (5) to produce an amine having the formula

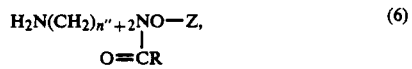
(6)

(e) condensing said compounds (4) and (6) to produce a compound having the formula

(7)

(f) hydrogenating said compound (7) to produce said tetraccordinate hydroxamate having the formula

(11)

4. A method for synthesizing an octacoordinate hydroxamate having the formula

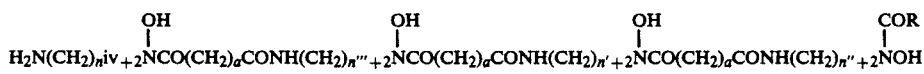

(a) reacting an aldehyde having the formula NC(CH$_2$)$_n$CHO (1), wherein n is an integer from 1 to 10 with an aminating agent having the formula Z—O—NH$_2$ wherein Z is an hydroxyl protecting group to produce an oxime having the formula NC(CH$_2$)$_n$CH=NO—Z (2), and reducing the oxime to produce a hydroxylamine having the formula NC(CH$_2$)$_{n+1}$NHO—Z (3), or (a-1) reacting a hydroxylamine having the formula Z—ONH—Q (A), wherein Z is an hydroxyl protecting group and Q is an amine protecting group, with an N-alkylating agent having the formula halo(CH$_2$)$_{n+1}$CN, wherein halo is halogen to produce a nitrile having the formula

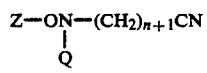

(B) and cleaving Q therefrom to produce said hydroxylamine (3), (b) condensing said hydroxylamine (3) with an anhydride having the formula

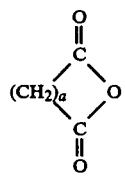

wherein a is an integer from 1 to 6 to produce a compound having the formula

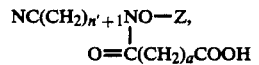

wherein n' is an integer from 1 to 10, (C) condensing said hydroxylamine (3) with an anhydride having the formula (RCO)$_2$O, wherein R is an alkyl group having from 1 to 6 carbon atoms or an aryl group to produce a compound having the formula

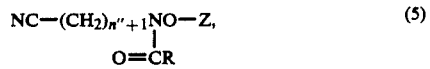

wherein n" may be the same as or different from n' and is an integer from 1 to 10, (d) reducing said compound (5) to produce an amine having the formula

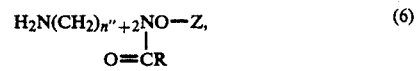

(e) condensing said compounds (4) and (6) to produce a compound having the formula

(f) reducing said compound (7) to produce an amine having the formula

(g) condensing said amine (8) with compound (4) to produce a nitrile having the formula

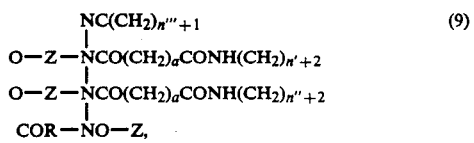

wherein n''' is an integer from 1 to 10 and may be the same as or different from n' and n", (h) reducing said nitrile (9) to produce an amine having the formula

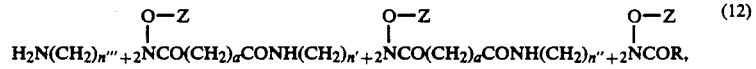

(i) condensing said amine (12) with an equivalent of said compound (4) to produce a nitrile having the formula

(j) reducing said nitrile (13) to produce said octaccordinate hydroxamate of the formula

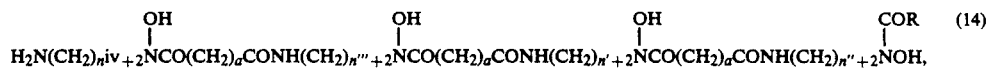

wherein n$^{iv}$ is an integer from 1 to 10 and may be the same as or different from n, n', n" and n''', a and R have the meanings set forth above.

5. A method for synthesizing an alkyl or aryl connected hydroxamate having the formula:

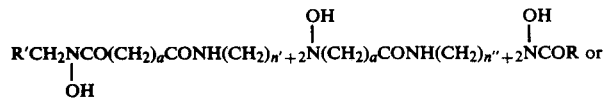

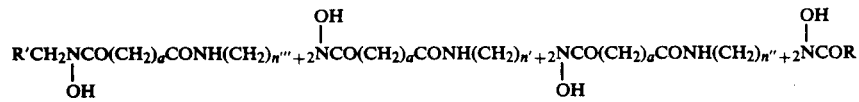

(a) reacting O-benzylhydroxylamine with an aldehyde of the formula R'—CHO, wherein R' is alkyl having from 1 to 20 carbon atoms; G—Y—(CH$_2$)$_x$—, wherein G is a removable protecting group, Y is —O— or —NH— and x is an integer from 1 to 20; or

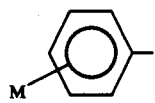

wherein M is —OG, —OR$_1$ (wherein R$_1$ is an alkyl group having from 1 to 20 carbon atoms), —COOH, or —NHG with an aminating agent having the formula Z—O—NH$_2$ wherein Z is an hydroxyl protecting group to produce an oxime having the formula R'CH=NO—Z (15) and reducing (15) to produce a hydroxylamine having the formula R'CH$_2$NHO—Z (16), (b) condensing said hydroxylamine (16) with an anhydride having the formula

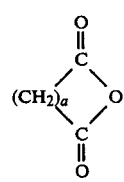

wherein a is an integer from 1 to 6 to produce a compound having the formula

 (17)

(c) condensing said compound (17) with said compounds (6), (8) or an amine having the formula

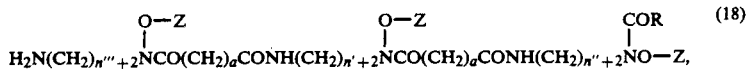 (18)

to produce compounds of the formulae:

 (19)

 (20)

and

 (21)

respectively, (d) reducing said compound (19), (20) or (21) to produce said corresponding hydroxamate having the formula:

$$\text{R'CH}_2\underset{\underset{\text{OH}}{|}}{\text{N}}\text{CO(CH}_2)_a\text{CONH(CH}_2)_{n''+2}\overset{\overset{\text{OH}}{|}}{\text{N}}\text{COR,} \quad (22)$$

$$\text{R'CH}_2\underset{\underset{\text{OH}}{|}}{\text{N}}\text{CO(CH}_2)_a\text{CONH(CH}_2)_{n'+2}\overset{\overset{\text{OH}}{|}}{\text{N}}(\text{CH}_2)_a\text{CONH(CH}_2)_{n''+2}\overset{\overset{\text{OH}}{|}}{\text{N}}\text{COR,} \quad (23)$$

or $$\text{R'CH}_2\underset{\underset{\text{OH}}{|}}{\text{N}}\text{CO(CH}_2)_a(\text{CONH(CH}_2)_{n'''+2}\text{NCO(CH}_2)_a\text{CONH(CH}_2)_{n'+2}\overset{\overset{\text{OH}}{|}}{\text{N}}\text{CO(CH}_2)_a\text{CONH(CH}_2)_{n''+2}\overset{\overset{\text{OH}}{|}}{\text{N}}\text{COR.} \quad (24)$$

UNITED STATES PATENT AND TRADEMARK OFFICE
CERTIFICATE OF CORRECTION

PATENT NO. : 4,987,253
DATED : January 22, 1991
INVENTOR(S) : Raymond J. Bergeron It is certified that error appears in the above-identified patent and that said Letters Patent is hereby corrected as shown below:

Title page, in item [63], under "Related U.S. Application Data" insert -- , both now abandoned -- after "Jun. 14, 1988"

Claim 3, column 15, after the formula, insert -- comprising: --

Claim 3, column 16, line 61, change "tetraccordinate" to
-- tetracoordinate --

Claim 4, column 17, after the formula, insert -- comprising: --

Claim 4, column 17, line 46, change "(C)" to -- (c) --

Claim 4, column 18, line 61, change "octaccor-" to
-- octacoor- --

Claim 5, column 19, before line 23, insert -- comprising: --

Claim 5, column 21, in the formula, delete the second "(" appearing therein.

Signed and Sealed this

Ninth Day of June, 1992

Attest:

DOUGLAS B. COMER

*Attesting Officer*   Acting Commissioner of Patents and Trademarks